United States Patent
Griffiths et al.

(10) Patent No.: US 7,621,887 B2
(45) Date of Patent: Nov. 24, 2009

(54) WET/DRY AUTOMATIC INJECTOR ASSEMBLY

(75) Inventors: Steven M. Griffiths, Ellicott City, MD (US); Robert L. Hill, Abingdon, MD (US); John G. Wilmot, Mount Airy, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 350 days.

(21) Appl. No.: 10/690,987

(22) Filed: Oct. 23, 2003

(65) Prior Publication Data

US 2004/0138611 A1 Jul. 15, 2004

Related U.S. Application Data

(63) Continuation-in-part of application No. 09/897,422, filed on Jul. 3, 2001, now Pat. No. 6,641,561, and a continuation-in-part of application No. 09/972,202, filed on Oct. 9, 2001, now Pat. No. 6,770,052.

(60) Provisional application No. 60/238,458, filed on Oct. 10, 2000, provisional application No. 60/238,448, filed on Oct. 10, 2000, provisional application No. 60/238,447, filed on Oct. 10, 2000.

(51) Int. Cl.
  *B65B 1/04* (2006.01)
  *A61M 37/00* (2006.01)
  *A61M 5/32* (2006.01)

(52) U.S. Cl. .......................... 604/89; 53/473; 604/191

(58) Field of Classification Search ............. 604/82–92, 604/131, 134, 135, 136, 139, 190, 191, 192, 604/132; 53/473–475
See application file for complete search history.

(56) References Cited

U.S. PATENT DOCUMENTS

| 3,592,245 A | 7/1971 | Schneller |
| 3,736,932 A | 6/1973 | Satchell |

(Continued)

FOREIGN PATENT DOCUMENTS

CH 446 620 11/1967

(Continued)

*Primary Examiner*—Kevin C Sirmons
*Assistant Examiner*—Elizabeth R Moulton
(74) *Attorney, Agent, or Firm*—Jones Day; Garry J. Tuma

(57) ABSTRACT

An automatic medicament injector having a compartment for a dry medicament component and a compartment for a wet medicament component. The two compartments are separated by a seal structure that has a plug that is moved from a sealing position into a mixing position when the device is activated. The seal structure includes a wiper that scrapes the interior walls in the dry component compartment to prevent the dry component from accumulating at the seal/glass interface. A tapered insert "funnels" the mixed medicament components to an attached needle assembly, but can be removed when the device is filled. A filter is provided between the medicament compartments and the needle assembly. A chamber between the filter and the needle assembly allows for better flow through the filter. An actuation assembly drives the plug into the mixing position and forces the mixed medicament through the needle and into the user.

22 Claims, 13 Drawing Sheets

U.S. PATENT DOCUMENTS

| | | | |
|---|---|---|---|
| 3,757,779 A | 9/1973 | Rovinski | |
| 3,807,119 A * | 4/1974 | Shields | 53/471 |
| 3,863,624 A | 2/1975 | Gram | |
| 3,938,513 A | 2/1976 | Hargest | |
| 4,043,335 A | 8/1977 | Ishikawa | |
| 4,060,082 A | 11/1977 | Lindberg et al. | |
| 4,215,701 A | 8/1980 | Raitto | |
| 4,266,557 A | 5/1981 | Merry | |
| 4,306,554 A | 12/1981 | Schwartz et al. | |
| 4,316,462 A | 2/1982 | Baker | |
| 4,413,991 A | 11/1983 | Schmitz et al. | |
| 4,529,403 A | 7/1985 | Kamstra | |
| 4,596,561 A | 6/1986 | Meyer et al. | |
| 4,599,082 A | 7/1986 | Grimard | |
| 4,613,326 A | 9/1986 | Szwarc | |
| 4,755,169 A | 7/1988 | Sarnoff et al. | |
| 4,781,701 A * | 11/1988 | Geprags | 604/240 |
| 4,792,329 A | 12/1988 | Schreuder | |
| 4,822,340 A | 4/1989 | Kamstra | |
| 4,861,335 A | 8/1989 | Reynolds | |
| 4,874,381 A | 10/1989 | Vetter | |
| 4,898,580 A | 2/1990 | Crowley | |
| 4,983,164 A | 1/1991 | Hook et al. | |
| 4,986,820 A | 1/1991 | Fischer | |
| 4,994,043 A | 2/1991 | Ysebaert | |
| 5,015,229 A | 5/1991 | Meyer et al. | |
| 5,041,088 A | 8/1991 | Ritson et al. | |
| 5,069,670 A | 12/1991 | Vetter et al. | |
| 5,080,649 A | 1/1992 | Vetter | |
| 5,125,892 A * | 6/1992 | Drudik | 604/89 |
| 5,281,198 A | 1/1994 | Haber et al. | |
| 5,295,965 A | 3/1994 | Wilmot | |
| 5,298,024 A | 3/1994 | Richmond | |
| 5,354,286 A | 10/1994 | Mesa et al. | |
| 5,364,369 A | 11/1994 | Reynolds | |
| 5,391,151 A | 2/1995 | Wilmot | |
| 5,397,048 A | 3/1995 | Konno et al. | |
| 5,429,603 A | 7/1995 | Morris | |
| 5,465,727 A | 11/1995 | Reinhold, Jr. | |
| 5,472,422 A | 12/1995 | Ljungquist | |
| 5,522,804 A | 6/1996 | Lynn | |
| 5,569,192 A * | 10/1996 | van der Wal | 604/84 |
| 5,620,421 A | 4/1997 | Schmitz | |
| 5,637,087 A | 6/1997 | O'Neil et al. | |
| 5,685,846 A * | 11/1997 | Michaels, Jr. | 604/90 |
| 5,704,918 A | 1/1998 | Higashikawa | |
| 5,713,857 A | 2/1998 | Grimard et al. | |
| 5,716,339 A * | 2/1998 | Tanaka et al. | 604/89 |
| 5,725,777 A | 3/1998 | Taylor | |
| 5,735,825 A | 4/1998 | Stevens et al. | |
| 5,785,683 A * | 7/1998 | Szapiro et al. | 604/89 |
| 5,795,337 A | 8/1998 | Grimard | |
| 5,807,344 A | 9/1998 | Iwasaki | |
| RE35,986 E | 12/1998 | Ritson et al. | |
| 5,865,798 A | 2/1999 | Grimard et al. | |
| 5,902,277 A | 5/1999 | Jentzen | |
| 5,971,953 A | 10/1999 | Bachynsky | |
| 6,053,895 A | 4/2000 | Kolberg et al. | |
| 6,080,131 A | 6/2000 | Van Der Meyden et al. | |
| 6,093,172 A | 7/2000 | Funderburk et al. | |
| 6,142,977 A | 11/2000 | Kolberg et al. | |
| 6,149,628 A | 11/2000 | Szapiro et al. | |
| 6,263,641 B1 * | 7/2001 | Odell et al. | 53/425 |
| 6,368,303 B1 | 4/2002 | Caizza | |
| 6,379,328 B1 | 4/2002 | Mac Clay | |
| 6,511,459 B1 | 1/2003 | Fago | |
| 6,602,223 B2 * | 8/2003 | Szapiro et al. | 604/89 |
| 6,807,797 B2 * | 10/2004 | Forsberg et al. | 53/440 |
| 2002/0049407 A1 | 4/2002 | Hill et al. | |
| 2003/0040701 A1 | 2/2003 | Dalmose | |
| 2004/0097874 A1 | 5/2004 | Griffiths et al. | |

FOREIGN PATENT DOCUMENTS

| | | |
|---|---|---|
| DE | 1 961 166 | 7/1970 |
| EP | 0 112 574 | 7/1984 |
| EP | 0 361 668 | 4/1990 |
| EP | 0 405 320 A2 | 1/1991 |
| EP | 0 511 183 A1 | 10/1992 |
| EP | 0 568 321 A2 | 11/1993 |
| FR | 2 604 363 | 4/1988 |
| FR | 2 741 810 | 6/1997 |
| WO | WO 94/09839 | 5/1994 |
| WO | WO96/01135 | 1/1996 |
| WO | WO01/93925 | 12/2001 |
| WO | WO 02/30494 A2 | 4/2002 |

* cited by examiner

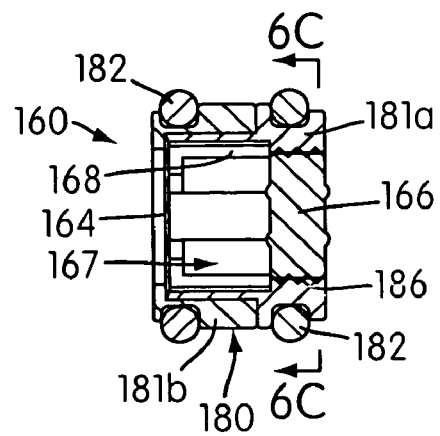
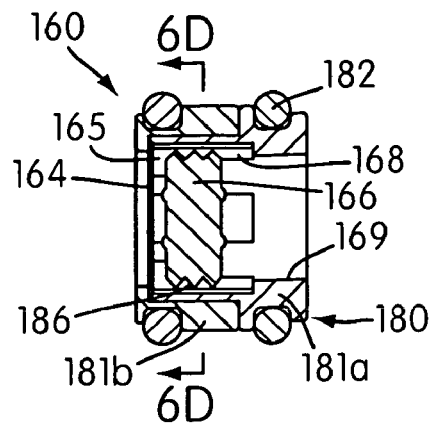
FIG. 6A          FIG. 6B
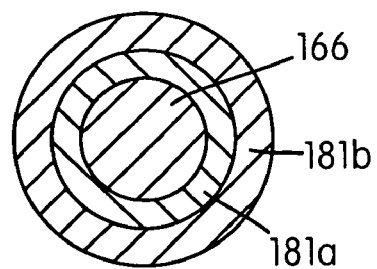
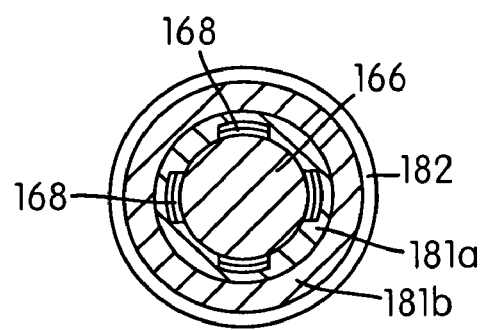
FIG. 6C          FIG. 6D

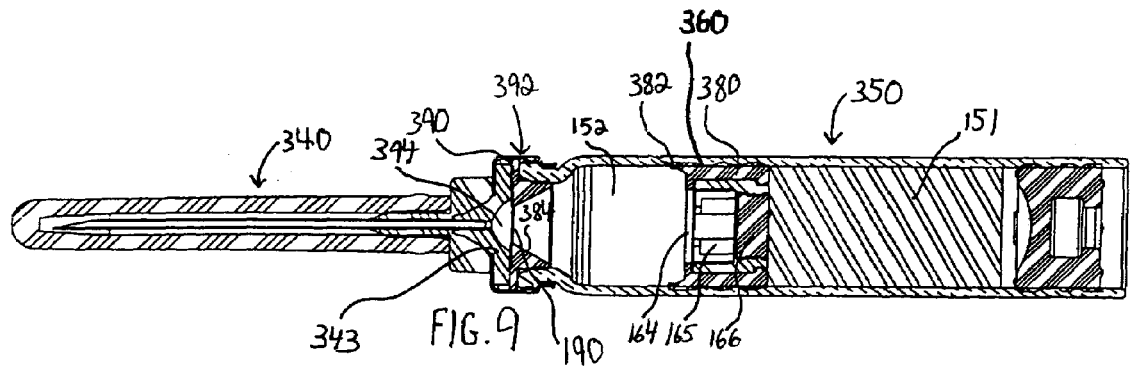
FIG. 9
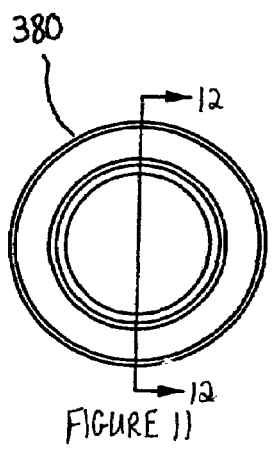
FIGURE 11
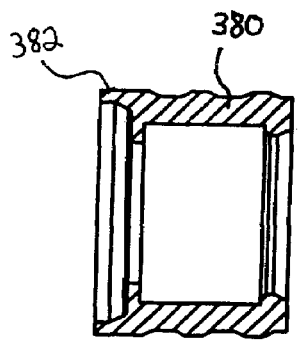
FIGURE 12
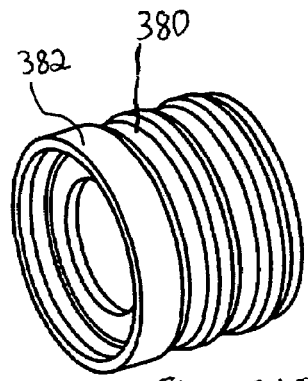
FIGURE 10
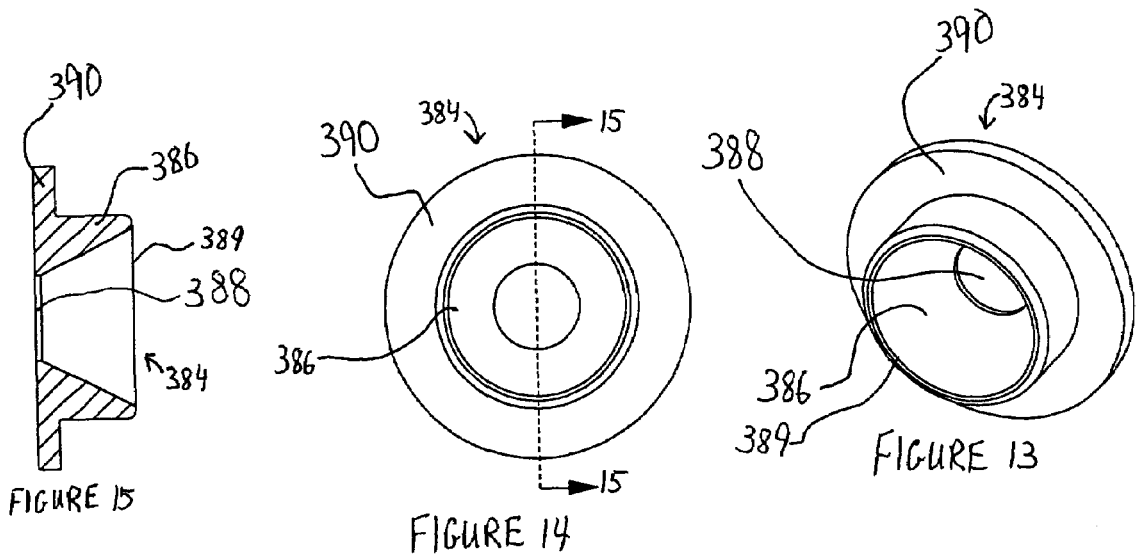
FIGURE 15
FIGURE 14
FIGURE 13

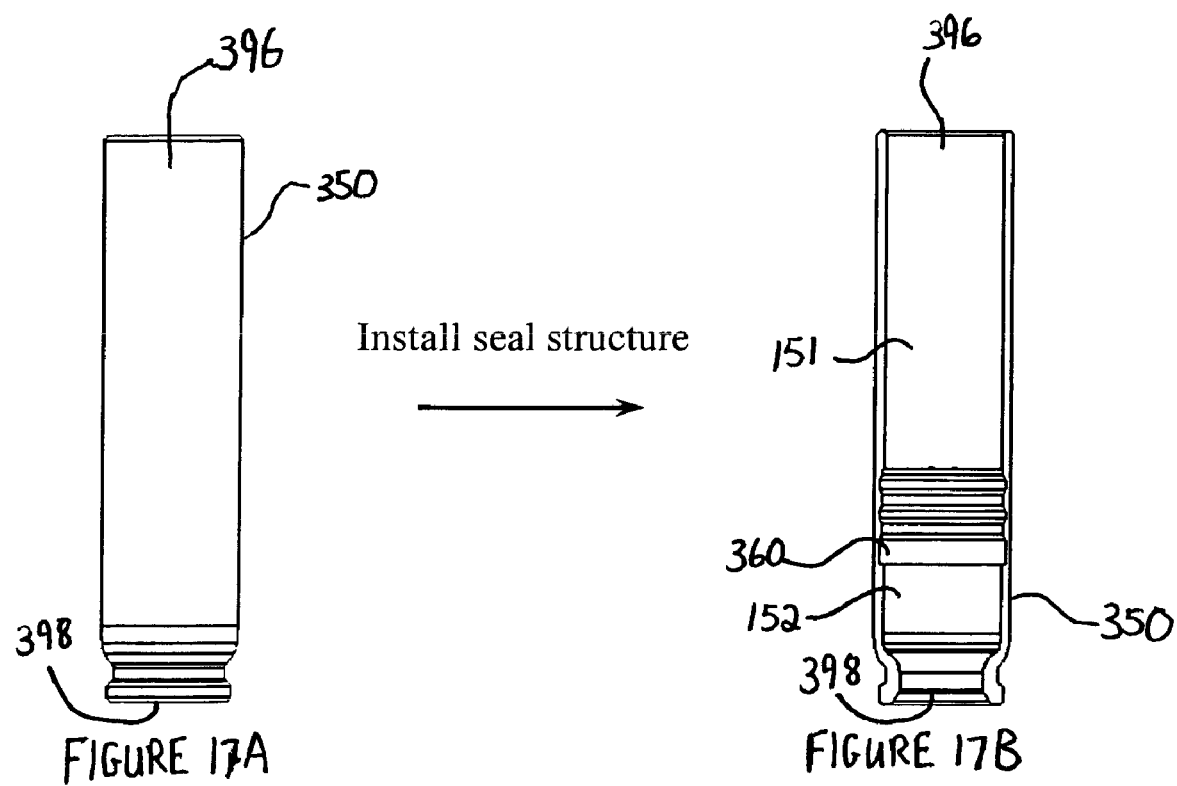

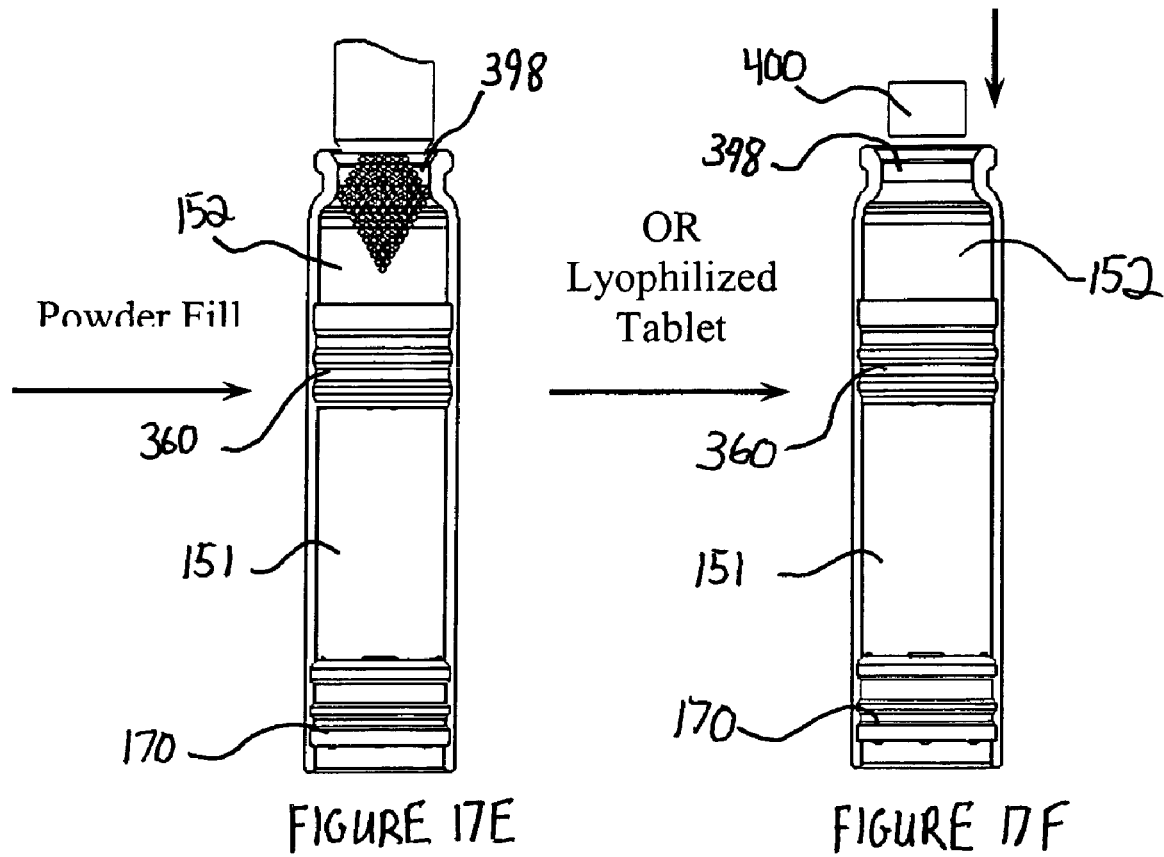

WET/DRY AUTOMATIC INJECTOR ASSEMBLY

CROSS-REFERENCE TO RELATED APPLICATIONS

This application is a continuation-in-part of U.S. patent application Ser. No. 09/897,422, filed on Jul. 3, 2001 now U.S. Pat. No. 6,641,561, and Ser. No. 09/972,202, filed on Oct. 9, 2001 now U.S. Pat. No. 6,770,052. Those two applications claim priority to U.S. Provisional Application Nos. 60/238,458, 60/238,448, and 60/238,447, all filed on Oct. 10, 2000. The contents of all of those applications are incorporated by reference herein in their entireties.

BACKGROUND OF THE INVENTION

1. Field of the Invention

The present invention relates to drug delivery devices. More particularly, the present invention relates to automatic injector assemblies capable of mixing two components of a medicament and then delivering the mixed medicament to an injection site.

2. Description of Related Art

An automatic injector is a device that enables intramuscular (IM) or subcutaneous administration of a dosage of medicament. Generally, the medicament is stored as a liquid formulation which is then injected intramuscularly. An advantage of automatic injectors is that they contain a measured dosage of a liquid medicament in a sealed sterile cartridge. As such, automatic injectors allow for quick and simple IM injection of a liquid medicament in emergency situations without the need for measuring dosages. Another advantage of automatic injectors is that the administration of the medicament is accomplished without the user initially seeing the hypodermic needle through which the medicament is delivered, and without requiring the user to manually force the needle into the patient. This is particularly advantageous when the medicament is being self-administered.

There are drawbacks associated with the long-term storage of medicament in a liquid formulation. For instance, some medicaments are not stable in solution and thus have a shorter shelf life than their solid counterparts. To address this concern, automatic injectors have been developed which store the medicament in solid form and mix the solid medicament with a liquid solution immediately prior to injection. These injectors, disclosed for example in U.S. Reissue Pat. No. 35,986, entitled "Multiple Chamber Automatic Injector," (the disclosure of which is incorporated herein specifically by reference), however, require the user of the injector to manually rupture a sealing member between the solid and liquid components and then manually shake the injector body to expedite dissolution of the solid component prior to injection. This increases the time needed to administer a dose of the medicament. However, rapid delivery of the medicament is needed in many emergency medical situations (e.g., nerve gas and chemical agent poisoning). Other wet/dry injection devices have been expensive to manufacture or provided unsatisfactory mixing of components prior to injection. Therefore, there is a need for a cost-effective automatic injector that stores medicament in solid form that does not require manual pre-mixing by the user.

SUMMARY OF THE INVENTION

One aspect of the invention relates to an automatic injection device containing a pre-loaded charge of medicament for automatically self-administering the medicament upon actuation thereof. The automatic injection device comprises a housing and a medicament chamber disposed in the housing. The medicament chamber includes a first compartment containing a dry medicament portion and a second compartment containing a wet medicament portion to be mixed with the dry medicament portion. A seal structure is provided between the first compartment and the second compartment. The seal structure is initially in a sealing condition that maintains the first compartment separate from the second compartment. The seal structure includes at least one flow path and an annular wiper portion disposed at the front end of the seal structure and positioned to movingly engage inner walls of the first compartment as the seal structure is moved through the first compartment. The wiper portion is configured to direct dry medicament particles engaged with the inner walls of the medicament chamber radially inwardly as the seal structure moves through the first compartment. The seal structure is converted to a mixing condition as a result of activation of the device. The automatic injection device also includes a needle assembly and an activation assembly. The needle assembly dispenses the mixed medicament portions from the medicament chamber. The activation assembly is carried by the housing and includes a stored energy source. Activation of the activation assembly releases the stored energy from the stored energy source, causing the seal structure to be converted from the sealing condition to the mixing condition, and thereby causing or allowing the medicament portions to be mixed and forced through the needle assembly.

Another aspect of the invention relates to an automatic injection device containing a pre-loaded charge of medicament for automatically self-administering the medicament upon actuation thereof. The automatic injection device comprises a housing and a medicament chamber disposed in the housing. The medicament chamber includes a first compartment containing a first medicament portion, and a second compartment containing a second medicament portion to be mixed with the first medicament portion. The device also includes a seal structure between the first compartment and the second compartment. The seal structure is initially in a sealing condition that maintains the first compartment separate from the second compartment, and is converted to a mixing condition as a result of activation of the device. A needle assembly dispenses the medicament charge from the medicament chamber. The needle assembly has a rearward opening with a diameter that is less than a diameter of the medicament chamber. An insert is mounted in a forward end of the medicament chamber adjacent the needle assembly. The insert defines a tapering flow pathway that tapers radially inwardly as it extends axially forwardly. An activation assembly is carried by the housing and includes a stored energy source. Activation of the activation assembly releases the stored energy from the stored energy source, causing the seal structure to be converted from the sealing condition to the mixing condition, and thereby causing or allowing the first and second medicament portions to be mixed, directed by the insert radially inwardly toward the rearward opening of the needle assembly, and forced through the needle assembly.

Yet another aspect of the invention relates to an automatic injection device containing a pre-loaded charge of medicament for automatically self-administering the medicament upon actuation thereof. The automatic injection device comprises a housing and a medicament chamber disposed in the housing. The medicament chamber includes a first compartment containing a first medicament portion, and a second compartment containing a second medicament portion to be mixed with the first medicament portion. The device also includes a seal structure between the first compartment and the second compartment. The seal structure is initially in a sealing condition that maintains the first compartment separate from the second compartment, and is converted to a mixing condition as a result of activation of the device. A needle assembly dispenses the medicament charge from the medicament chamber. A filter is positioned between the medicament chamber and the needle assembly. The needle assembly comprises a needle and a needle support for mounting the needle to the medicament chamber. The needle support defines a needle assembly chamber having a rearward opening covered by the filter. The needle assembly chamber has an inner surface tapering radially inwardly as it extends axially forwardly toward a rearward end of the needle. The device also has an activation assembly carried by the housing that includes a stored energy source. Activation of the activation assembly releases the stored energy from the stored energy source, causing the seal structure to be converted from the sealing condition to the mixing condition, and thereby causing or allowing the first and second medicament compounds to be mixed and forced through the needle assembly.

A further aspect of the invention relates to a method of filling an automatic injection device. The method comprises filling a front compartment of a chamber within the automatic injection device with a dry medicament compound from a front end of the chamber. The method also comprises filling a rear compartment of the chamber with a wet medicament portion from a rear end of the chamber. The rear compartment is separated from the front compartment by a seal structure. Finally, the method comprises sealing the rear compartment of the chamber, placing a tapered insert in the front end of the chamber, and attaching a needle assembly to the front end of the chamber. The tapered insert has a tapered flow pathway which is tapered such that the diameter increases as it extends rearwardly.

These and other aspects and advantages of the invention will be described below.

BRIEF DESCRIPTION OF THE DRAWINGS

The invention will be described in conjunction with the following drawing figures, in which like reference numerals designate like elements, and in which:

FIG. 6A is a longitudinal cross-sectional side view of a seal structure in accordance with another embodiment of the present invention, wherein the movable sealing plug is in a closed sealing position blocking the flow of the liquid injection solution;

FIG. 6B is a longitudinal cross sectional side view of seal structure similar to 6A, but showing the movable sealing plug in an open by-pass position permitting the flow of the liquid injection solution;

FIG. 6C is a lateral cross sectional view of the seal structure of the present invention taken through the line 6C-6C in FIG. 6A;

FIG. 6D is a lateral cross sectional view of the seal structure of the present invention taken through the line 6D-6D in FIG. 6B;

FIG. 9 is a longitudinal cross-sectional view of a chamber and needle assembly according to a further embodiment of the invention;

FIG. 10 is a perspective view of an outer sealing member in the chamber and needle assembly of FIG. 9;

FIG. 11 is a front elevational view of the outer sealing member of FIG. 10;

FIG. 12 is a longitudinal sectional view of the outer sealing member of FIG. 10, taken through Line 12-12 of FIG. 11;

FIG. 13 is a perspective view of a tapered insert in the chamber and needle assembly of FIG. 9;

FIG. 14 is a front elevational view of the tapered insert of FIG. 13;

FIG. 15 is a longitudinal sectional view of the tapered insert in the chamber and needle assembly of FIG. 13, taken through Line 15-15 of FIG. 14;

FIGS. 17A-17F are sectional and partially sectional views of a chamber illustrating a process for filling it with dry and liquid medicament components.

DETAILED DESCRIPTION

In the following description, the present invention is described in connection with a push button type auto injector, whereby the user removes an end cap assembly and presses a button to trigger the injection process. The present invention, however, is not limited to push button type automatic injectors; rather, it is contemplated that the present invention may be incorporated into a nose activated auto injector, as described for example in U.S. Pat. No. 5,354,286, the disclosure of which is hereby incorporated herein by reference for such teaching.

Figure 1:
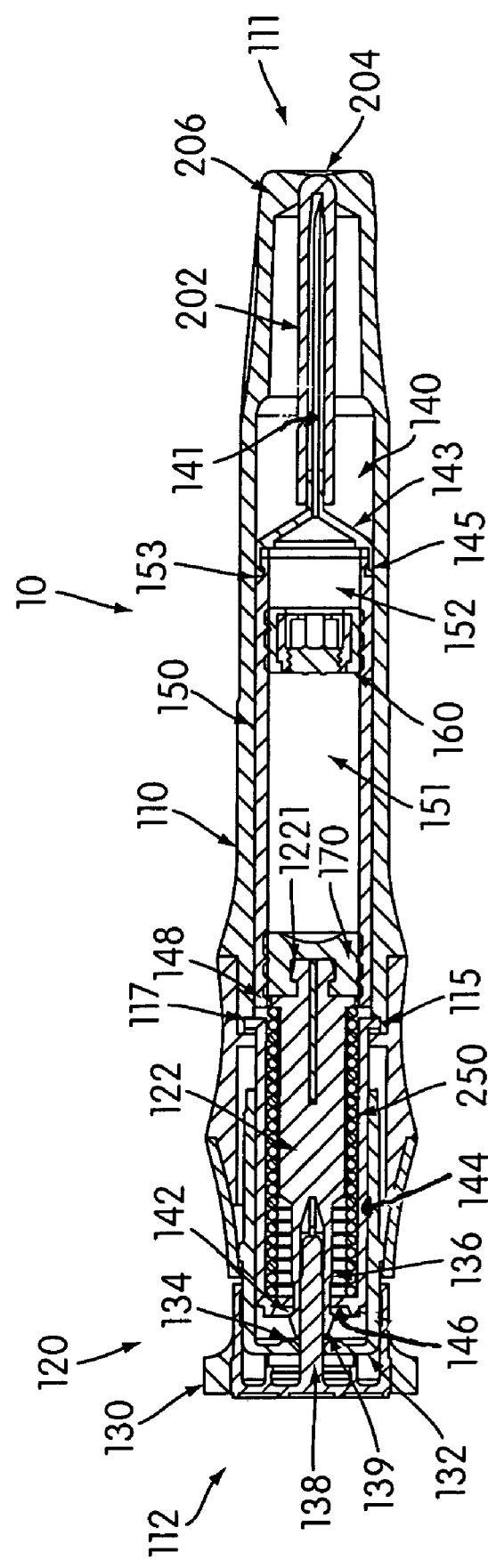
FIG. 1 is a longitudinal cross-sectional view of a wet/dry automatic injector assembly in accordance with an embodiment of the present invention.

FIG. 1 is a longitudinal cross-sectional view of an automatic injector assembly 10 in accordance with an embodiment of the present invention. The automatic injector assembly 10 includes a generally hollow tubular plastic housing 110. Generally, the housing 110 includes an injection end 111 and an activation end 112, as shown in FIG. 1. In the embodiment shown, an actuator assembly 120 is inserted into the rearward end of the housing 110. The actuator assembly 120 is received within the housing 110 until flange 115 of a sleeve member 144 is captured within an annular groove 117 on the interior surface of housing 110. A removable safety cap 130 is releasably secured to the actuator assembly 120.

The actuator assembly 120 may be of any conventional type as known in the art, such as that disclosed in commonly assigned U.S. Pat. No. 5,391,151 hereby incorporated by reference. The present invention employs a rear-end activating device, similar to that in the aforementioned U.S. Pat. No. 5,391,151, and is therefore only briefly described herein. The actuator assembly 120 includes an activation button sleeve 132 having internal activation surfaces 134. The activation assembly further includes a plastic collet 122 with a split rearward portion forming spring fingers 136 as known in the art. The safety cap 130 has a pin portion 138 that extends between the spring fingers 136 so as to keep them spread apart when the injector is in a storage condition. The spring fingers 136 terminate in semi-conical configurations including rearwardly facing sloping surfaces 139 and forwardly facing flat surfaces 142. The collet 122 is surrounded by a cylindrical sleeve 144 having inwardly extending flange 146 at the rearward end thereof. The collet 122 has a forward annular flange 148. A coil spring 250 surrounds the collet 122 and is compressed between the flange 148 and flange 146. The collet flat surfaces 142 are retained in engagement with the rearwardly facing surfaces of the flange 146, and thus prevented from moving off of the flange surfaces by the pin 138 when the injector is stored.

To activate the injector, the safety pin 130 is manually pulled off of the rear end of the injector, thus removing pin 138 from between the fingers 136. The activation button 132 can then be pushed inwardly, and as a result of the activation surfaces thereof, 134 engages the sloping surfaces 139 of the spring fingers 136. This forces the spring fingers 136 inwards toward one another and off of the retaining surfaces of the flange 146. The compressed spring 250 is then free to release the stored energy therein to move the collet 122 forwardly under the force of the spring to affect an injection operation as will be described later in more detail.

The actuator assembly 120 may be of any type known in the automatic injector art that employs releasable stored energy. For example, rather than employing a spring, it may employ a charge of compressed gas.

Located within the interior of the housing 110 is a vial or chamber 150, preferably made of glass, for containing both a liquid injection solution and a dry medicament, or other types of medicament portions, as appropriate. The chamber 150 is preferably a hollow cylinder, with a smooth cylindrical inner surface. The liquid injection solution is located within a wet portion or compartment 151 of the chamber 150. The dry medicament is located within a dry portion 152 or compartment of the chamber 150. It is contemplated that the dry medicament may be in powder, lyophilized, freeze-dried, or any other solid formulation known in the art. A seal structure 160 engages the interior side walls of the chamber 150 to seal the dry portion 152 from the wet portion 151 and to prevent seepage of the liquid injection solution into the dry portion 152 prior to activation of the injector assembly. Further, a needle assembly 140 mounts to the forward end of vial or chamber 150 to inject the medicament upon activation of the injector assembly. In this embodiment, the forward end portion of the chamber 150 has an annular groove 153 formed therein for attachment of the needle assembly 140. The needle assembly 140 includes a funnel-shaped needle support 143. The wide end of the needle support 143 has an annular rib 145 that is snap-fit into groove 153 to form a seal with the chamber 150. The needle support 143 can be made of a resilient plastic material, or metal with a rubber seal that seats into groove 153. The forward narrow end 147 (see FIG. 2A) of the needle support 143 sealingly receives the rearward end of hollow needle 141. The needle support 143 forms a sealed fluid channel from the chamber 150 to the needle 141. A rubber needle sheath 202 surrounds the needle 141 and receives the narrow end 147 of the needle support 143. A filter 190 is sealingly retained across the entire wide-end mouth of the needle support 143 by an annular sealing washer 156. Alternatively, the filter 190 could be ultrasonically welded or otherwise secured to the needle support 143.

Figure 2A:
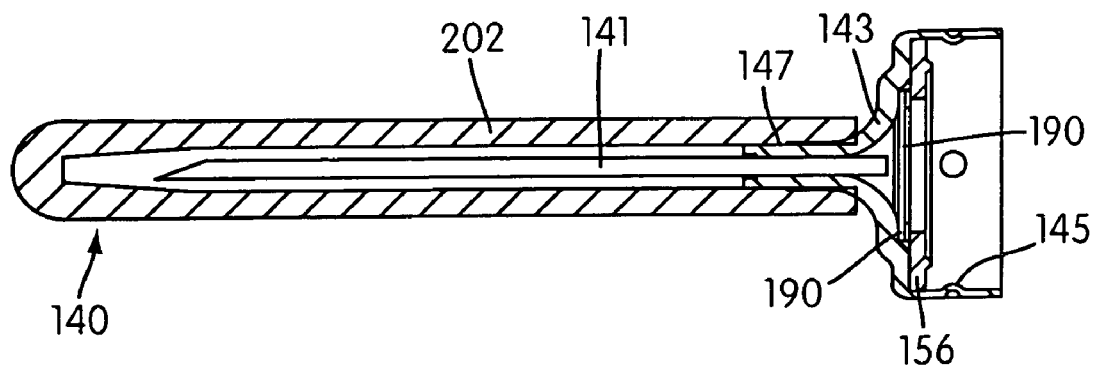
FIGS. 2A-2B illustrate longitudinal cross-sectional views of needle support assemblies in accordance with certain embodiments of the present invention.
Figure 2B:
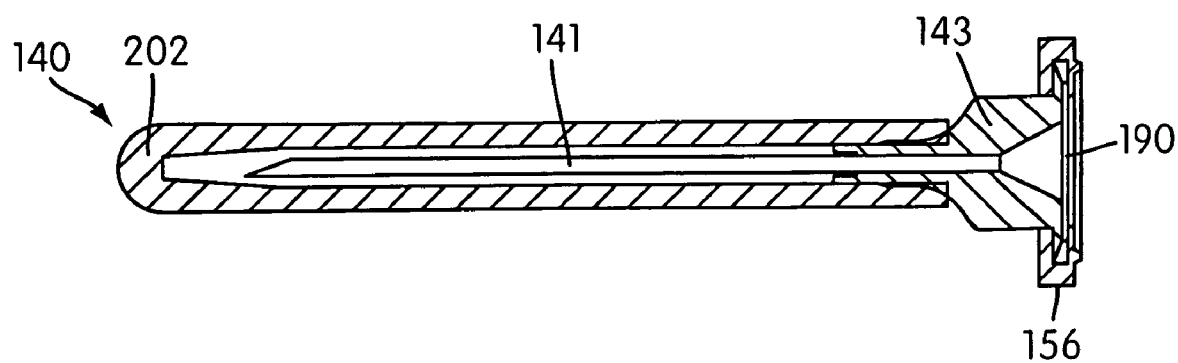
Figure 3A:
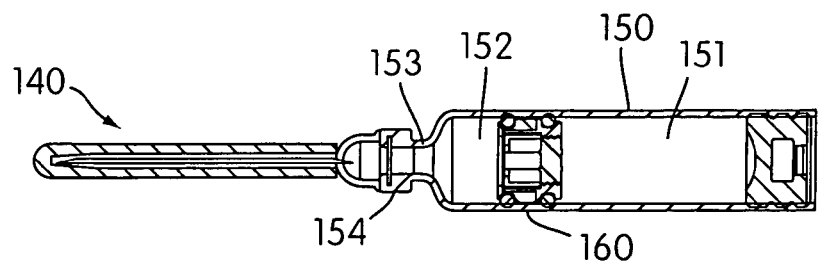
FIGS. 3A-3D illustrate cross-sectional side views of various cartridge or chamber configurations and corresponding needle assembly options according to certain embodiments of the present invention.
Figure 4:
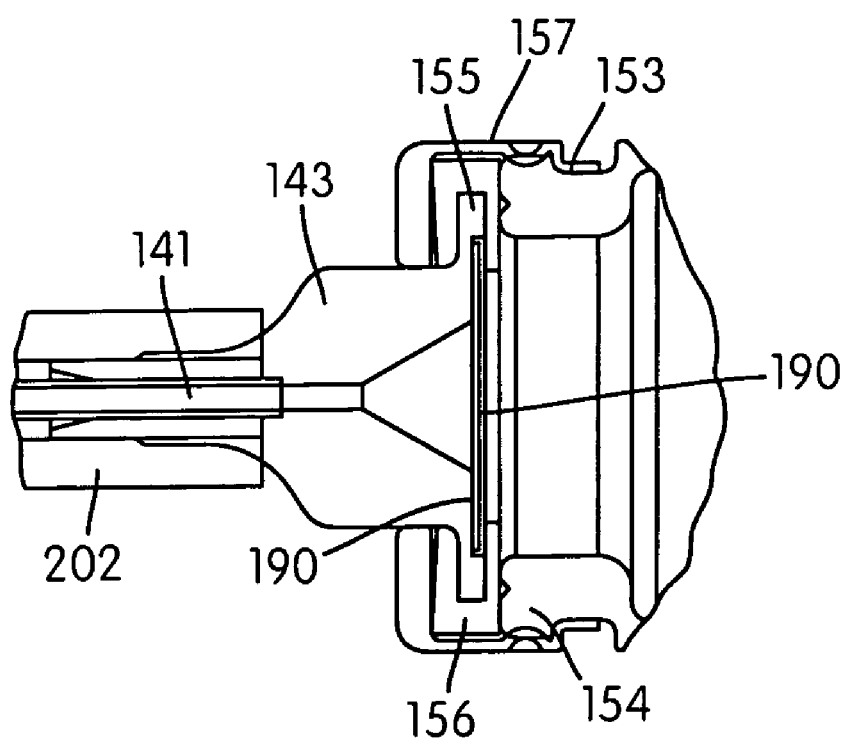
FIG. 4 is an enlarged partial cross-sectional side view of a needle assembly/cartridge engagement according to another embodiment.

FIGS. 2B, 3A, and 4 illustrate another embodiment of a needle assembly 140 and chamber 150. The chamber 150 in this embodiment is known in the art as a dental cartridge. The dental cartridge has a cylindrical rear portion and a narrowed forward neck portion defining an outer annular groove 153. The forward end of the dental cartridge defines an annular flange portion 154. In this embodiment, the needle support 143 has a rearward annular flange 155 that receives an annular sealing member 156 that surrounds both sides of flange 155. The sealing member 156 serves to seal a filter 190 over the wide end of the funnel shaped needle support 143. The rearward surface of the sealing member 156 is sealingly clamped against the forward surface of chamber flange 154 by a metal retaining clamp 157 as best seen in FIG. 4.

As shown in FIG. 1, forward end 1221 of the collet 122 extends into the rearward end of chamber 150 and is adapted to connect with a plunger 170 rearwardly sealing the wet container 151. The plunger 170 is adapted to sealingly engage the side wall of the wet container 150 to prevent leakage of the contents (e.g., liquid injection solution) of the wet container 151. The plunger 170 is preferably formed from a material having low frictional properties such that the collet 122 and plunger 170 may easily slide within the wet container 150 when operated. Alternatively, the plunger 170 may be lubricated with silicone or other suitable non-reactive lubricant. The movement of the collet 122 and the plunger 170 pressurizes the liquid located within the wet container 151. A suitable medicament is located within a dry container 152.

Figure 3B:
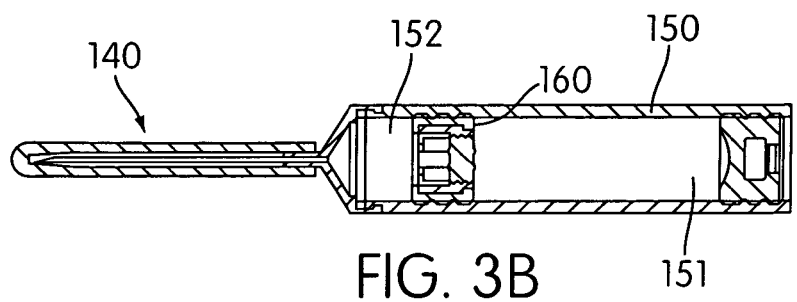
Figure 3C:
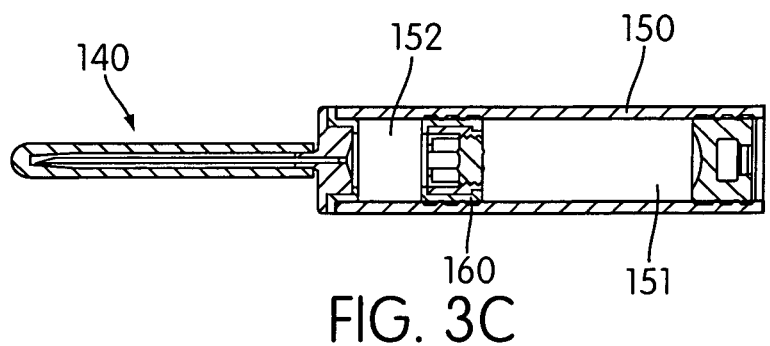
Figure 3D:
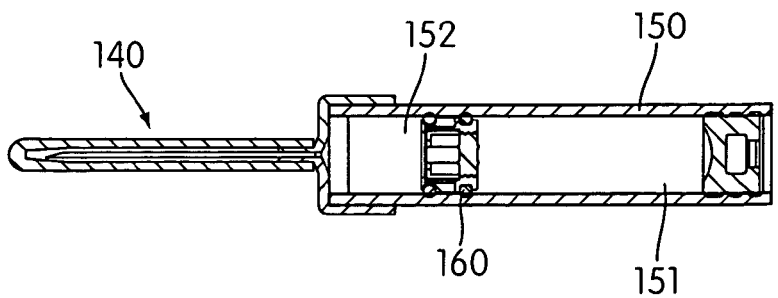

The embodiment of FIGS. 1 and 2A is advantageous in that it has an open mouth configuration wherein the needle-end of the vial or chamber is not significantly narrowed or tapered. Such an open mouth configuration permits direct access to the dry portion 152 of chamber 150 for easy loading. Further, the open mouth configuration aids in preventing cross contamination between wet portion 151 and dry portion 152 in that the dry portion 152 does not have to be filled through liquid portion 151 of chamber 150. Needle assembly 140 can be mounted to vial or chamber 150 in a snap-on configuration (FIG. 3B), an internal mount configuration (FIG. 3C), or an external needle assembly configuration (FIG. 3D).

As mentioned above, the seal structure 160 is adapted to engage the interior side walls of chamber 150 to prevent passage of the contents (e.g., liquid injection solution) of wet portion 151 into the dry portion 152 prior to activation of the automatic injection assembly. Generally, seal structure 160 can include an outer sealing member 180, a movable sealing plug 166, a by-pass zone 165, at least one flow path 167, and preferably also includes a filter or membrane 164. With reference to FIGS. 5A-D, seal structure 160 can preferably be formed as a six piece (FIG. 5A), five piece (FIG. 5B), four piece (FIG. 5C), or three piece (FIG. 5D) configuration.

Figure 5A:
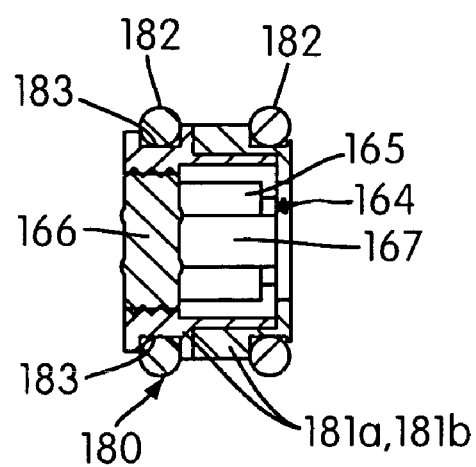
FIGS. 5A-5D illustrate cross-sectional side views of various embodiments of a seal structure according to the present invention.

More particularly, with reference to FIG. 5A, the outer sealing structure 180 of the six piece configuration can comprise a two piece annular rigid body 181 wherein members 181a, 181b thereof are formed into the two piece rigid body using, e.g., annular weld connections or other bonding techniques known in the art. Outer sealing structure 180 can further include multiple external sealing members 182, e.g., two O-rings, to provide an annular sealing engagement with the inner wall of vial or compartment 150. The sealing structure 180 further includes an internal plug member 166 and a filter or dispersion membrane 164 as will be discussed in greater detail later.

Figure 5B:
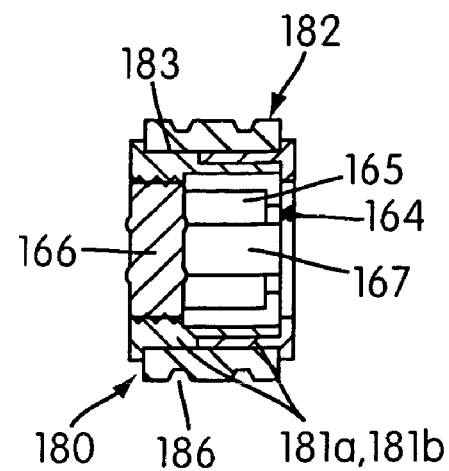

In another embodiment, as shown in FIG. 5B, rather than plural O-rings, outer sealing structure 180 can include a single external sealing member 182, e.g., a unitary gasket, to provide an annular sealing engagement with the inner wall of vial or compartment 150. External sealing member 182 may optionally be secured to two piece rigid body 181 using any bonding techniques known in the art. Further, rigid body members 181a, 181b may be shaped such that they securingly engage external sealing members 182 within notched recesses 183. Alternately, sealing members 182 may be secured to rigid body members 181a, 181b by an interference fit. As with the first embodiment, a filter or membrane 164 is clamped in place at the proximal end of flow path 167 between member 181a and member 181b of the two piece rigid body.

Figure 5C:
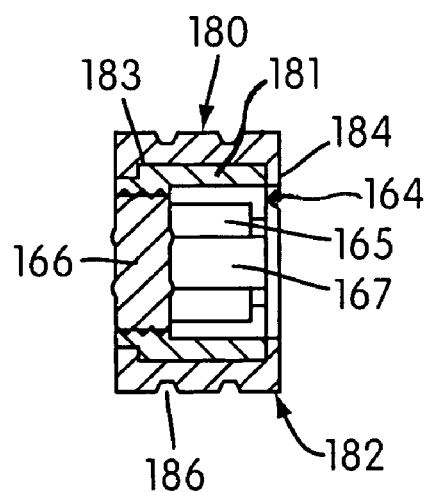
Figure 5D:
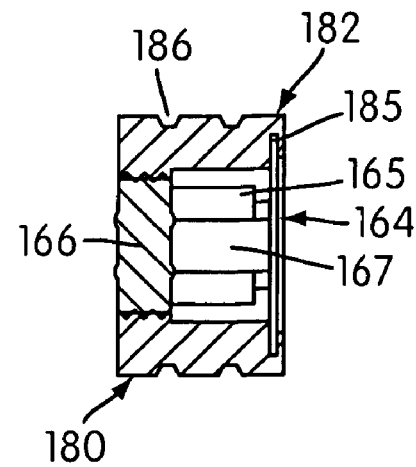

In another embodiment, as shown in FIG. 5C, outer sealing structure 180 comprises a unitary internal rigid member 181 and an external sealing member 182. Again, internal rigid member 181 and external sealing member 182 may optionally be secured together using any bonding techniques known in the art. Further, internal rigid member 181 and external sealing member 182 may be formed such that they securingly engage each other using a combination of notched recesses 183 and extending shoulders 184. The filter or membrane 164 can be held in place between internal rigid member 181 and shoulder 184 of external sealing member 182. Alternatively, the filter 164 may be ultrasonically welded or otherwise secured to the rigid member 181. In yet another embodiment, as shown in FIG. 5D, outer sealing object 180 can comprise a unitary external sealing member 182 which can optionally be molded so as to accommodate filter or member 164 within retaining recess 185. FIGS. 6A and 6B illustrate another embodiment that is very similar to that of FIG. 5A, but provides a slightly different shape for outer annular rigid body 181 and particularly the members 181a, 181b thereof.

In each embodiment illustrated in FIGS. 5A-5D and 6A-6B, external sealing member 182 is preferably formed from a non-reactive elastomer material which can provide for the necessary sealing engagement with the inner wall of vial or compartment 150. Further, external sealing member 182 can optionally be lubricated with silicon or other suitable non-reaction lubricant to facilitate movement of the outer sealing object 180 forwardly within vial or compartment 150 upon receiving sufficient force as will be described. The movable sealing plug 166 is preferably formed from a material, such as an elastomer or PTFE, having low frictional properties such that the sealing plug 166 may easily slide within outer sealing object 180 when the injector is activated. The movable sealing plug 166 may also optionally be lubricated with silicon or other suitable non-reactive lubricant. In the embodiments illustrated, and as specifically shown in FIG. 6B, it is preferred that the outer annular structure 180 defines an inner surface having a smooth cylindrical configuration towards the rearward portion 169 thereof, and longitudinally extending grooves 168 towards the forward portion thereof. The grooves 168 create a flowpath or flowpaths 167 through which liquid in the wet compartment 151 can bypass seal plug 166 when the plug 166 is moved forwardly from sealing engagement with cylindrical surface portion 169 into the grooved portion 168. The movement of the sealing plug 166 into the by-pass area 165 opens the fluid flow path 167 between wet portion 151 and dry portion 152. The movable sealing plug 166 preferably includes a plurality of circumferential grooves 186 to provide for enhanced sealing engagement and to facilitate sliding action of the plug 166.

As mentioned above, the seal structure 160 preferably includes filter or membrane 164 at the end of flow path 167 through which the liquid injection solution may pass after the injector has been activated. The liquid injection solution then enters the dry portion 152 of the chamber 150 where it mixes with and dissolves the dry medicament. More particularly, the filter 164 disperses the liquid injection solution exiting the seal structure 160 to present laminar fluid flow to the full surface of the dry medicament, thereby wetting the entire surface of the dry medicament for rapid and complete dissolution. The filter membrane 164 can be any structure that generally uniformly distributes the liquid across the entire diameter of the chamber 150 for enhanced dissolution of the dry medicament.

During operation, manual activation of the actuator assembly 120 releases the collet 122 (as described above), which applies pressure on the plunger assembly 170. The application of pressure on the plunger assembly 170 by the collet and spring assembly 124 moves the plunger 170 in the direction of the needle assembly 140. As a result, the entire chamber 150 and needle assembly 140 are moved forwardly in the housing 110 such that needle 141 pierces through the front end of sheath 202 and exits through the forward end of the housing 110, and particularly through a hole 204 in the front nose-cone portion 206 of the housing. The sheath 202, which serves to maintain the needle 141 sterile when the injector is in storage, also serves as a shock absorber during activation as it is compressed in generally accordion like fashion between the nose cone 206 and needle support 143.

When the needle 141 is extended from the housing 110 and the chamber 150 and needle support 143 approach the nose cone 206 portion of the housing so that further forward movement of chamber 150 is substantially resisted, the plunger 170 then begins to travel forwardly through the chamber 150. This pressurizes the liquid injection solution located within the wet compartment 151. With reference to FIGS. 6A-6B, the increased pressure within the wet compartment 151 moves the sealing plug 166 from a first sealed position wherein sealing plug 166 is sealingly engaged with surface 169 of outer sealing structure 180 (FIG. 6A) to a second by-pass position (FIG. 6B) that allows the injection solution to flow through flow path 167 created by grooves 168 and thereby through seal structure 160.

As described above, the high pressure developed within the wet portion 151 in response to movement of the collet 122 and the plunger assembly 170 forces the liquid injection solution through the seal structure 160 dissolving the drug into a medicament injection solution which will then be forced out through the needle 141 and into the patient. As the collet 122 and plunger assembly 170 continue forward, the plunger 170 will eventually contact the seal structure 160, which, in a preferred embodiment, causes the seal structure 160 to move in the direction of the needle assembly 140. Movement of the seal structure 160 would cause any remaining solution within the portion 152 to be dispersed through the needle assembly 140, so as to reduce the amount of residual medicament remaining within the chamber 150.

As shown in FIGS. 2A, 2B and 4, a membrane or filter 190 is preferably provided adjacent the needle assembly 140 to prevent any dry medicament particles from clogging the rearward end of needle 141 prior to an injection operation. The membrane 190 may also serve to slightly restrict or slow injection of medicament into the patient, to facilitate more thorough dissolution during injection.

More particularly, to prevent the passage of undissolved dry medicament to the needle assembly 140, a medicament support 190 is preferably provided between the end of the dry compartment 152 and the needle assembly 140. The support 190 can serve to prevent blockage of the needle assembly 141 by preventing the dry medicament from entering the area surrounding the needle assembly 140 while permitting passage of the mixture of dissolved medicament and liquid injection solution. The support 190 may be configured as described in U.S. Provisional Application No. 60/238,448, which is herein incorporated by reference in a manner consistent with this disclosure. It is contemplated that multiple supports 190 may be located within the dry compartment 152. The provision of the supports 190 may also improve the laminar flow of the liquid injection solution through the dry medicament thereby improving dissolution.

Further, a diaphragm assembly (not shown) may also be provided adjacent the medicament support 190, as known in the art. The diaphragm assembly acts to prevent the passage of the liquid injection solution to the needle assembly 140 prior to activation of the actuator assembly 120. More particularly, the diaphragm assembly will not rupture until either the butt end of the needle assembly 140 ruptures the expanded diaphragm or sufficient pressure builds in the dry compartment 160 to rupture the diaphragm, again as known in the art.

As described above, the movement of the collet 122 causes the injection needle 141 of the injection assembly 140 to advance and protrude through the housing 110. As such, the injection of the medicament can be performed with a simple operation. In sum, the user simply removes the end cap assembly 130, locates the injection end of the housing 110 adjacent the injection site, and presses the push button 132. This operation automatically triggers the operation of the drive assembly or spring 250 to advance the collet 122 causing the liquid injection solution located within the wet portion 151 to enter the dry portion 152 through the seal structure 160. The dissolved medicament is then transmitted through the injection needle 141 to provide the user with the necessary dose of medicament. The automatic injector 10 in accordance with the present invention reduces the amount of time required to administer medicament compared to other wet/dry injectors and eliminates the need for mixing by the user.

The seal structure 160 advantageously enables the manufacture of a superior wet/dry auto injector with a complementary combination of components that are either known in the art of conventional auto-injectors or are otherwise relatively simple to manufacture. The seal structure 160 enables sufficient mixing of wet and dry medicament components without requiring manual shaking. This mixing action is enhanced by the filter or membrane 164. In a preferred embodiment, the filter 164 is a supported, hydrophobic acrylic copolymer cast on a non-woven nylon support. Preferably, it is a FlouRepel treated membrane for superior oleophobicity/hydro-phobicity.

Figure 7:
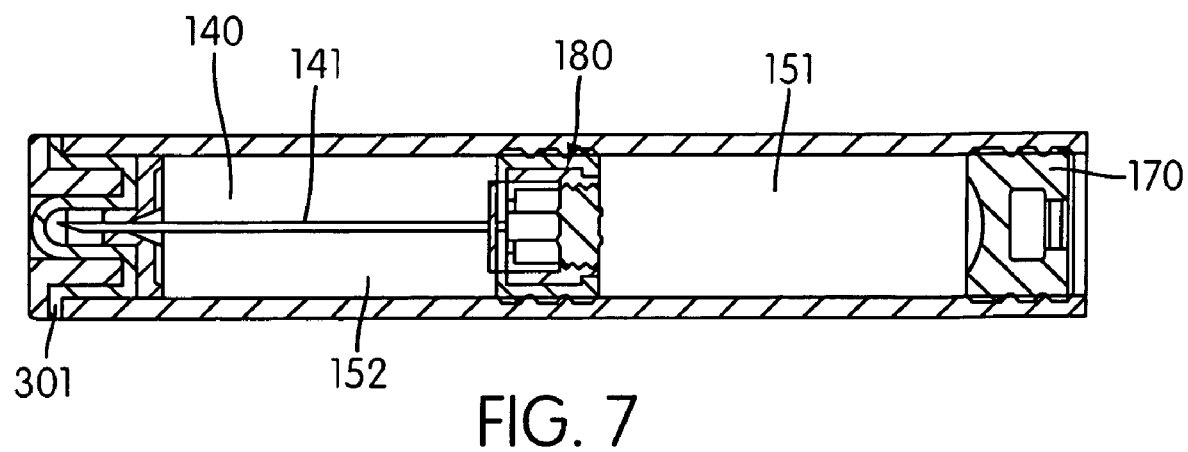
FIG. 7 is a longitudinal cross-sectional view of a wet/dry automatic injector cartridge or chamber configuration in accordance with another embodiment of the present invention.

In another embodiment, shown in FIG. 7, the automatic injector cartridge includes a needle assembly 140 located within the dry portion 152. The needle assembly 140 extends within the dry portion 152 to the sealing structure 180, described above in connection with FIGS. 5A-5D. The sealing structure 180 separates the dry portion 152 from the wet portion 151. As shown in FIG. 7, the cartridge further includes a plunger 170 positioned therein. The plunger 170 is configured to engage the collet 122 of the activation assembly 120. The cartridge includes a sheath 301. Like the sheath 202, the sheath 301 maintains the needle 141 in a sterile environment until it projects from the end of the sheath 301 in response to activation of the activation assembly 120. During operation, the needle assembly 140 passes through the dry portion 152 as the wet medicament passes through the sealing structure 180.

In other embodiments (see FIGS. 8A and 8B), no inner plug 166 is provided. Rather, the outer structure 180 is simply complemented by a seal membrane 226 that extends across the inner area defined by the inner surface of the outer structure. When the chamber 150 reaches the forward end of the housing during an injection operation, pressurization of the wet compartment 151 causes the seal membrane 226 to rupture, thereby allowing the seal structure 160 to permit liquid to pass therethrough. In this embodiment, it may be desirable to provide the seal structure 160 with a pointed member 228 disposed adjacent to the seal membrane 226 to facilitate rupturing of the seal membrane upon pressurized expansion thereof during an injection operation. The member 232 on which the pointed member 228 is mounted has a plurality of passages 234 that permits fluid to pass therethrough. Filter or membrane 164 is preferably mounted distal to the passages 234 to present laminar or distributed flow to the dry medicament.

EXAMPLES

An injector according to the present invention was loaded with liquid injection solution and dry medicament and activated with the follow results.

| Loaded | | Dispensed | | |
| --- | --- | --- | --- | --- |
| Dry Powder | Fluid | Dry Powder | Fluid | Operational Time |
| Mg | Ml | % | mg | ml | Secs. |
| 531 | 2.7 | 94 | 497 | 2.3 | 4.0 |
| 557 | 2.7 | 93 | 515 | 2.3 | 4.5 |
| 582 | 2.6 | 92 | 537 | 2.2 | 4.4 |

Other embodiments and modifications of the invention are also contemplated. For example, a cover assembly, described for example in U.S. Pat. No. 5,295,965 (the disclosure of which is specifically incorporated herein by reference) may be secured to the injection end of the housing 110 after deployment of the medicament. Furthermore, the automatic injector may further include a nipple plunger assembly, as described for example in U.S. Pat. No. 5,713,866 (the disclosure of which is specifically incorporated herein by reference).

In yet a further embodiment, the forward dry chamber 152 contains the needle 141, as shown in FIG. 7. The needle 141 is forced through a forward plug stopper upon initial compression of the two chamber system. As known in the art, providing the needle 141 in the forward chamber 152 provides improved longitudinal compactness of the design.

In yet another embodiment, a pre-filled syringe is provided with the seal structure disposed between wet and dry components.

In further contemplated embodiments, the seal structure 160 can be used in the same type of injector described herein, except rather than employing a dry (powder) medicament separated by a liquid component, a first liquid medicament is separated from a second fluid component by the seal structure 160. In yet another embodiment, the seal structure 160 can be used in what is known in the art as a "needleless injector" where an injection can be made into a patient without a needle or cannula.

FIG. 9 is a longitudinal cross-sectional view of a chamber 350 mounted to a needle assembly 340 according to a further embodiment of the invention. Neither a housing 110 nor an actuator assembly 120 is shown in FIG. 9; however, the chamber 350 and needle assembly 340 may be used with the housings 110 and actuator assemblies 120 described above or with substantially any known housing or actuator assembly.

In the chamber 350 and needle assembly 340 shown in FIG. 9, many of the components are the same as those described above with respect to FIG. 1; therefore, the description above will suffice for those components.

Figure 8A:
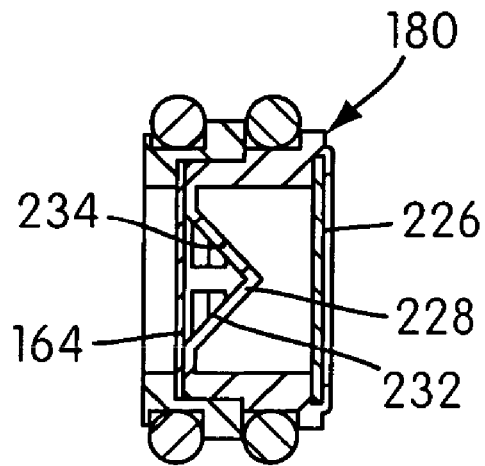
FIGS. 8A and 8B are longitudinal cross sectional views of two additional embodiments of seal structures in accordance with the present invention.
Figure 8B:
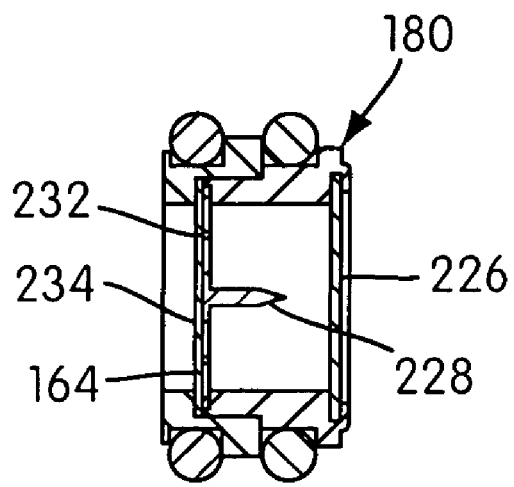

Like the chamber 150, the chamber 350 has a wet portion or compartment 151 and a dry portion or compartment 152. A sealing structure 360 separates the wet portion 151 and the dry portion 152. The sealing structure 360 includes an outer sealing member 380, a moveable sealing plug 166, a by-pass zone 165, and may also include a filter or dispersion membrane 164. Although a moveable sealing plug 166 is shown in FIG. 9, the sealing structure 360 may include a rupturable seal membrane 226 instead of a sealing plug 166, as shown in FIGS. 8A and 8B.

FIG. 10 is a perspective view of the outer sealing member 380. FIG. 11 is a front elevational view of the sealing member 380, and FIG. 12 is a sectional view of the outer sealing member 380 taken through Line 12-12 of FIG. 11. As shown, the outer sealing member 380 has an annular wiper portion 382 that makes sealing contact with the inner wall of the dry portion 152 of the chamber 350 and extends axially forwardly, in the direction of actuating movement along the longitudinal axis of the chamber 350, toward the needle assembly 140.

While the outer sealing members 180 that were described above do form a seal with the inner wall of the container 150, during the actuation process, powder from the dry medicament in the dry portion 152 tends to accumulate around the sealing member 180, 380 at the seal/container interface. As the device actuates, some of the powder that accumulates around the sealing member 180, 380 can be driven or forced into the space between the glass and the sealing member 180. The entire area around and between the sealing member 180 and the inner wall of the container 150 can become a "dead space," in which accumulated powder cannot properly mix with fluid.

The wiper portion 382 helps to eliminate the accumulation of powder around the sealing member 380 by "wiping" or "scraping" any accumulated powder away from the wall of the chamber 350 and directing it radially inwardly, where it can properly mix with the wet medicament portion as the sealing member 380 passes through the dry portion 152. As shown in FIG. 9, the wiper portion 382 makes contact with the inner wall of the dry portion 152 of the chamber 350 along substantially the entirety of its length. The extent of contact between the wiper portion 382 and the inner wall of the dry portion 152 is possible, at least in part, because the wiper portion 382 extends axially. Although it would be possible to construct a wiping structure that extended radially or angularly outward from the main body of the sealing member 380, such a wiping structure would not be in contact with the inner wall of the dry portion 152 over substantially the entirety of its length. Therefore, it would be possible for such a putative wiping structure to cause an undesirable accumulation of medicament powder, particularly if medicament powder were to move past it and into the space between it and the inner wall of the dry portion 152. Accordingly, the straight, forwardly-extending wiper portion 382 is currently preferred.

A wiper portion 382, although shown in the embodiment of FIG. 9, may be used in any of the embodiments shown and described above and in any variations thereof.

As shown in FIG. 9, the chamber 350 has an "open mouth" configuration; i.e., the container itself does not taper substantially as it meets the needle assembly 340 (for example, as compared with the embodiment shown in FIG. 3A). The advantages of having an "open mouth" container were described above with respect to the container 150. If the "mouth" of the container (i.e., the opening into the dry portion 152 of the container) is open and wide, it becomes easier to load the dry component of the medicament. However, having a tapered portion adjacent to the needle assembly 340 helps to direct the medicament radially inwardly, toward the needle assembly 340, when the injection is taking place.

In order to realize the advantages of an "open mouth" container and the advantages of a tapered container, the chamber 350 includes a tapered insert 384 at its mouth, just behind the needle assembly 340. FIG. 13 is a perspective view of the tapered insert 384, FIG. 14 is a front elevational view, and FIG. 15 is a sectional view through Line 15-15 of FIG. 14.

The tapered insert 384 tapers radially inwardly as it extends axially forwardly, such that it forms a funnel portion 386 with a small central opening 388 at one end. The tapered insert 384 also has a rearward open end 389 with a larger open diameter. The insert 384 sealingly engages the walls of the chamber 350. Extending radially outward from the outer surface of the funnel portion 386 proximate to the small central opening 388 is an annular sealing flange 390. In the embodiment shown in FIGS. 13-15, the annular sealing flange 390 is an integral portion of the tapered insert 384. However, in some embodiments, the annular sealing flange 390 may be joined to the funnel portion 386 by adhesives or other securing methods. Additionally, as will be described in more detail below, in some configurations, the annular sealing flange 390 may be absent. The insert 384 is preferably formed from a material that will not react with the dry medicament stored in the compartment 152.

The chamber 350 and needle assembly 340 include a metallic skirt, generally indicated at 392, that is rolled or crimped so as to capture or secure the needle assembly 340 to the front end of the chamber 350. In this embodiment, the annular sealing flange 390 fits between the chamber 350 and needle assembly 340 so as to form a seal between them. Either the annular sealing flange 390 itself or, depending on the configuration, the entire tapered insert 384 may be made of an elastomeric or other rubber material suitable for sealing.

The tapered insert 384 may be removed from the chamber 350 in order to effect the loading of the dry medicament and then inserted into the chamber 350 prior to joining with the needle assembly 340. Although the tapered insert 384 is shown with a funnel portion 386 of constant, radially inward taper, the tapering of the tapered insert 384 may be of any type that will facilitate fluid flow from the chamber 350 into the needle assembly 340.

At the forward end of the tapered insert 384, the small, central opening 388 in the insert 384 is covered by a filter 190 that is positioned between the tapered insert 384 and the needle support 343 to filter fluids passing from the chamber 350 into the needle assembly 340, so as to prevent any undissolved medicament from entering the needle assembly 340. Forward of the filter 190, defined by the rearward (container-facing) side of the needle support 343 is a chamber 394 that tapers radially inwardly toward its forward end. The chamber 394 is contoured to expose a substantial portion of the surface area of the filter 190 to the flow between the chamber 350 and the needle assembly 340. Preferably, the chamber 394 has an opening at least as large as the small central opening 388 in the tapered insert 384. In the embodiment shown in FIG. 9, the chamber 394 is substantially hemispherical, although other configurations may be used. The chamber 394 can be seen more clearly in FIG. 16, which is a longitudinal cross-sectional view of a portion of the needle assembly 340. The chamber 394 allows greater, more laminar, and more fully developed flow through the filter 190 to the needle 141. Furthermore, the chamber 394 is shaped to direct the flow of medicament to the needle 141.

Figure 16:
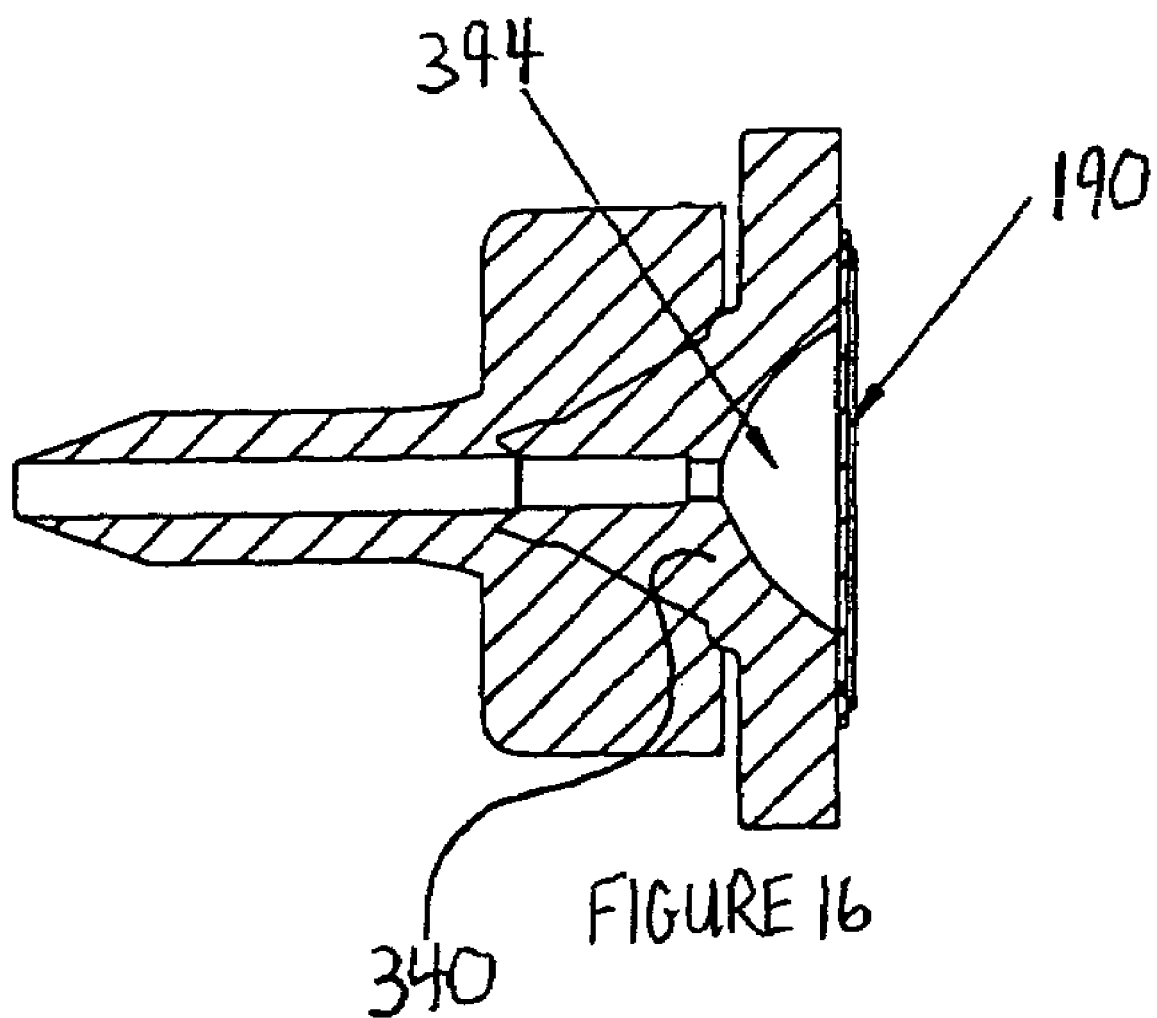
FIG. 16 is a longitudinal sectional view of a portion of the needle assembly of FIG. 9, illustrating a chamber behind the needle assembly filter.

As is also shown in FIG. 16, neither the needle 141 nor any other structure protrudes into the chamber 394. Although it would be possible to construct a chamber 394 and needle assembly such that a portion of the end of the needle protruded into the chamber 394, such an arrangement might cause turbulent flow around the end of the needle that protruded into the chamber 394, or might otherwise eliminate some of the benefits of the chamber 394.

The sealing member 380 with wiper portion 382, tapered insert 384, and chamber 394 may all be used in a wet/wet autoinjector assembly that includes two fluid medicament components. In a wet/wet autoinjector assembly, a burstable membrane is typically positioned over the opening of the compartment adjacent to the needle assembly, in order to prevent fluid in that compartment from leaking out of the compartment and into the needle assembly. If the sealing member 380, tapered insert 384, and chamber 394 are provided in a wet/wet autoinjector assembly, a burstable membrane may be provided as a portion of the tapered insert 384. For example, the burstable membrane could be positioned in the funnel portion 386 of the insert.

The sealing member 380, tapered insert 384, and chamber 394 may also be used in a wet/dry or wet/wet autoinjector assembly that does not include all of the features described above. For example, the tapered insert 384 and chamber 394 may be used in any wet/dry or wet/wet autoinjector in order to improve the loading and dispensing performance of the autoinjector.

A chamber for an autoinjector may be filled with appropriate medicament components in several different ways. For example, one common way to fill an autoinjector chamber is to fill a first medicament (e.g., a wet medicament) through an opening in the chamber and then fill a second medicament (e.g., a dry medicament) through that same opening in the chamber. This process, while common, tends to cause cross-contamination because both wet and dry medicaments are filled through the same opening. For example, if a dry powder medicament is filled first, any powder that accumulates around the opening may mix with a subsequently-filled wet medicament, thereby contaminating the contents of the wet compartment. Conversely, if the wet medicament is filled first, liquid that accumulates around the opening may mix with some of the subsequently-filled dry medicament, thereby contaminating the contents of the dry compartment.

However, using a chamber 150, 350 according to the invention, it is advantageous to fill the chamber 150, 350 using a separate opening in the chamber 150, 350 for each type of medicament, thus eliminating the cross-contamination problem. This sort of filling process for a chamber 150, 350 includes a number of tasks and will be described below with respect to the chamber 350, although the described process is, in general, equally applicable to the other embodiments described above. Ordinarily, the filling process would be performed in an aseptic environment.

Typically, the chamber 350 is initially open at both ends and does not include any interior structures, as shown in FIG. 17A. A seal structure, such as seal structure 360, is first inserted into the chamber 350 so that it is positioned substantially as shown in FIG. 17B.

Figure 17C:
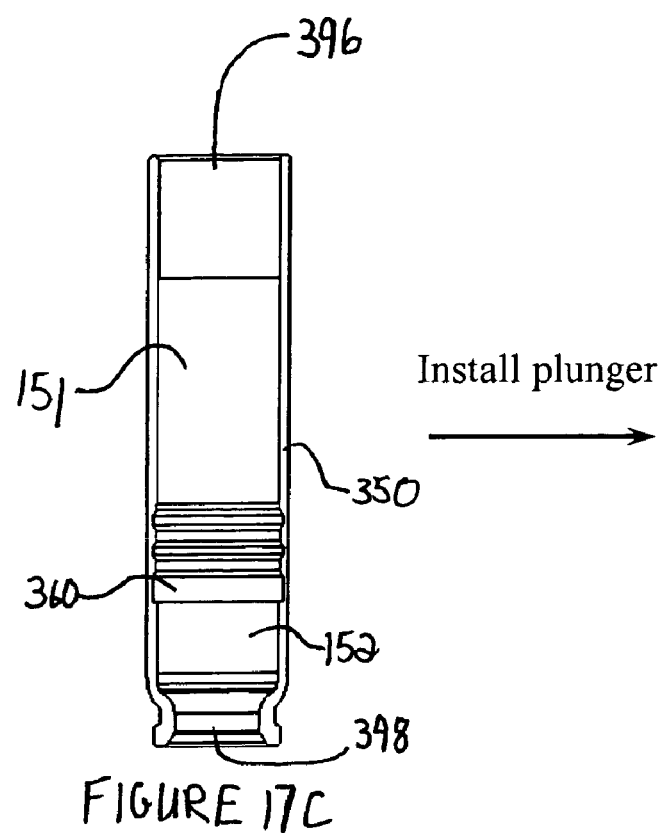
Figure 17D:
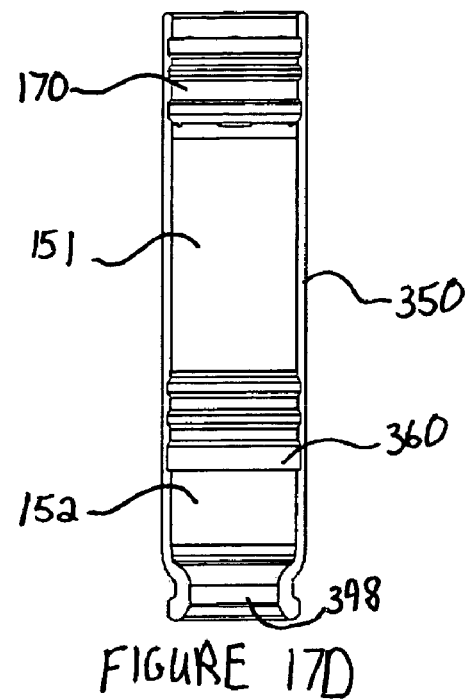

Once the seal structure 360 is in place, the chamber 350 is removed to or placed in a low particulate aseptic environment, and is positioned so that the wet portion or compartment 151 can be filled through an opening 396 in the rear end of the chamber 350, as shown in FIG. 17C. (The low particulate environment prevents possible cross-contamination of the wet portion 151.) After the wet portion 151 is filled, the opening 396 in the rear end of the chamber 350 is sealed by installing the plunger 170, as shown in FIG. 17D. The placement of the chamber 350 in a low particulate environment prior to filling the wet portion 151 helps to prevent contamination of the wet portion 151 by powder or other particulates.

Once the wet portion 151 is filled with the desired liquid medicament portion and the rear end is sealed with the plunger 170, the chamber 350 is removed from the low particulate environment and is placed in an appropriate aseptic environment so that the dry portion or chamber 152 of the chamber 350 can be filled through an opening 398 in the front of the chamber 350. There are two common ways of filling the dry portion 152. One way to fill the dry portion 152 is to place a dry powder directly into the dry portion 152 through the opening 398, as shown in FIG. 17E.

Another way to fill the dry portion 152 is to fill the dry portion 152 with a liquid medicament through the opening 398 and then lyophilize the liquid medicament directly in the dry portion 152 to leave only the desired dry medicament. While this process of liquid filling and lyophilizing may be used, it sometimes leaves residues in the dry portion 152, which may interfere with the stability of the dry medicament or otherwise contaminate it.

A third way to fill the dry portion 152 is to lyophilize a liquid medicament in a separate container to form a lyophilized dry medicament tablet 400 and then deposit the dry medicament tablet 400 in the dry portion 152 through the opening 398, as shown in FIG. 17F. This variation of the filling process is used most advantageously with a chamber that has a relatively wide opening into its dry portion, so that tablets of various sizes can be accommodated. If a chamber has a relatively narrow opening into its dry portion, it may be necessary to fill that dry portion with powder, or to lyophilize a liquid medicament directly in the dry portion to form a dry powder.

After the dry portion 152 is filled, a tapered insert 384 is placed in opening 398 of the chamber 350 and the needle assembly 340 is secured over the tapered insert 384. When the process is complete, the chamber 350 is as shown in FIG. 9.

Although the present invention has been described with respect to a number of embodiments, those embodiments are meant to be illustrative, rather than limiting. As those of ordinary skill in the art will understand, modifications and variations are possible within the scope of the appended claims.

What is claimed is:

1. A method of loading a chamber of an automatic injection device with a medicament, the method comprising:
    inserting a first seal structure into the chamber at a user selected location within the chamber to divide the chamber into a front compartment and a rear compartment, the chamber having an open front end forming an open end of the front compartment and an open rear end forming an open end of the rear compartment, the chamber having no interior structures, the first seal structure initially sealing the front compartment from the rear compartment and having a moveable sealing plug operative to move within the first seal structure to open a flow path through the first seal structure around the outermost periphery of the sealing plug;
    filling the rear compartment of the chamber with a wet medicament portion through the rear end of the chamber, the wet medicament portion contacting interior side walls of the chamber;

sealing the rear end of the chamber with a second seal structure movable toward the front compartment to force the wet medicament portion into the front compartment to mix with a dry medicament portion as the second seal structure moves toward the front compartment;

filling the front compartment of the chamber with the dry medicament portion through the front end of the chamber;

placing a tapered insert in the front end of the chamber, the tapered insert having a constant radially-inward taper extending from the rearward end of the insert to the front end of the insert, the constant radially-inward taper forming a tapered flow pathway through the insert, the insert having a rearward opening that forms a common boundary with the chamber, the rearward opening having a diameter that equals an inside diameter of the chamber where the rearward opening forms the common boundary; and sealing the front end of the chamber.

2. The method of claim 1, wherein placing a tapered insert in the front end of the chamber comprises abutting an annular flange of the tapered insert against an outside edge of the front end of the chamber.

3. The method of claim 1 wherein sealing the front end comprises attaching a needle assembly to the front end.

4. The method of claim 1, wherein the rear compartment of the chamber is filled with the wet medicament portion before the front compartment of the chamber is filled with the dry medicament portion.

5. The method of claim 1, wherein sealing the rear end comprises installing a plunger.

6. The method of claim 1, wherein the dry medicament portion is a powder.

7. The method of claim 1, wherein the dry medicament portion is a tablet sized to fit through the front end of the chamber.

8. The method of claim 7, wherein the tablet is prepared by lyophilizing a liquid suspension or solution containing suspended or dissolved dry medicament portion in a separate container.

9. The method of claim 1 further comprising after inserting a first seal structure and before filling the rear compartment:

placing the chamber in a low particulate environment.

10. The method of claim 9 further comprising after sealing the rear end of the rear compartment and before filling the front compartment:

removing the chamber from the low particulate environment; and placing the chamber in an aseptic environment.

11. A method of loading a chamber of an automatic injection device with a medicament, the method comprising:

inserting a needleless seal structure into the chamber to divide the chamber into a front compartment and a rear compartment, the chamber having an open front end forming an open end of the front compartment and an open rear end forming an open end of the rear compartment, the seal structure initially sealing the front compartment from the rear compartment and having a moveable sealing plug operative to move from a sealing position to a by-pass area within the seal structure to open a flow path through the seal structure, the open front end of the chamber having an open mouth configuration;

placing the chamber in a low particulate environment;

filling the rear compartment of the chamber with a wet medicament portion through a rear end of the chamber, the wet medicament contacting interior side walls of the chamber;

sealing the rear end of the chamber;

removing the chamber from the low particulate environment;

placing the chamber in an aseptic environment;

filling the front compartment of the chamber with a dry medicament portion through a front end of the chamber;

placing a tapered insert in the front end of the chamber, the tapered insert having a constant radially-inward taper extending from a large opening at one end of the insert to a small opening at an opposite end of the insert that forms a tapered flow pathway through the insert, the large opening having a diameter that equals an inside diameter of the chamber where the large opening forms a common boundary with the chamber; and sealing the front end of the chamber.

12. The method of claim 11, wherein placing a tapered insert in the front end of the chamber comprises abutting an annular flange of the tapered insert against an outside edge of the front end of the chamber.

13. The method of claim 11 wherein sealing the front end comprises attaching a needle assembly to the front end.

14. The method of claim 11, wherein the rear compartment of the chamber is filled with the wet medicament portion before the front compartment of the chamber is filled with the dry medicament portion.

15. The method of claim 11, wherein filling the front compartment of the chamber with a dry medicament comprises:

filling the front compartment with a liquid; and lyophilizing the liquid to leave only the dry medicament in the chamber.

16. The method of claim 11, wherein sealing the rear end comprises installing a plunger.

17. A method of loading a chamber of an automatic injection device with a medicament, the method comprising:

inserting a seal structure into the chamber at a user selected location within the chamber to divide the chamber into a front compartment and a rear compartment, the seal structure initially sealing the front compartment from the rear compartment and having a slidable sealing plug operative to slide from a sealing position to a by-pass area within the seal structure to open a flow path through the seal structure, the chamber having no interior structures and an open front end forming an open end of the front compartment and an open rear end forming an open end of the rear compartment, the open front end and the open rear end each having an open mouth configuration;

filling the rear compartment of the chamber with a wet medicament portion through the open mouth configuration at the rear end of the chamber;

sealing the rear end of the chamber;

filling the front compartment of the chamber with a dry medicament portion through the open mouth configuration at the front end of the chamber;

placing a tapered insert in the front end of the chamber, the tapered insert comprising a funnel portion of constant radially-inward taper having a small opening at one end of the insert and a large opening at an opposite end of the insert, the funnel portion forming a tapered flow pathway through the insert, the large opening forming a common boundary with the chamber, the large opening having a diameter that equals an inside diameter of the chamber where the large opening forms the common boundary; and sealing the front end of the chamber.

18. The method of claim 17, wherein placing a tapered insert in the front end of the chamber comprises abutting an annular flange of the tapered insert against an outside edge of the front end of the chamber.

19. The method of claim 17, wherein sealing the rear end comprises installing a plunger.

20. The method of claim 17, wherein the front compartment of the chamber is filled with the dry medicament portion before the rear compartment of the chamber is filled with the wet medicament portion.

21. The method of claim 17, wherein the seal structure has an outer sealing member that forms a seal with the inner wall of the container.

22. The method of claim 17, further comprising attaching a needle assembly to the front end.

* * * * *

UNITED STATES PATENT AND TRADEMARK OFFICE
CERTIFICATE OF CORRECTION

PATENT NO. : 7,621,887 B2 Page 1 of 1
APPLICATION NO. : 10/690987
DATED : November 24, 2009
INVENTOR(S) : Griffiths et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 635 days.

Signed and Sealed this

Twenty-sixth Day of October, 2010

David J. Kappos
*Director of the United States Patent and Trademark Office*